(12) United States Patent
Riebel et al.

(10) Patent No.: US 10,660,521 B2
(45) Date of Patent: May 26, 2020

(54) MEASUREMENT SYSTEM FOR MEASURING THE CONCENTRATION OF AN ANALYTE WITH A SUBCUTANEOUS ANALYTE SENSOR

(71) Applicant: Roche Diabetes Care, Inc., Indianapolis, IN (US)

(72) Inventors: Stefan Riebel, Mannheim (DE); Kai-Oliver Schwenker, Haßloch (DE); Ralf Schmitz, Weinheim (DE); Carsten Mueglitz, Schoenau (DE); Thomas Eissenloeffel, Heidelberg (DE)

(73) Assignee: ROCHE DIABETES CARE, INC, Indianapolis, IN (US)

( * ) Notice: Subject to any disclaimer, the term of this patent is extended or adjusted under 35 U.S.C. 154(b) by 356 days.

(21) Appl. No.: 15/575,472

(22) PCT Filed: Jun. 3, 2016

(86) PCT No.: PCT/EP2016/062673
§ 371 (c)(1),
(2) Date: Nov. 20, 2017

(87) PCT Pub. No.: WO2016/193444
PCT Pub. Date: Dec. 8, 2016

(65) Prior Publication Data
US 2018/0184905 A1    Jul. 5, 2018

(30) Foreign Application Priority Data
Jun. 3, 2015 (EP) .................................. 15170388

(51) Int. Cl.
*A61B 5/00* (2006.01)
*A61M 5/172* (2006.01)
(Continued)

(52) U.S. Cl.
CPC ............ *A61B 5/0022* (2013.01); *A61B 5/002* (2013.01); *A61B 5/1451* (2013.01);
(Continued)

(58) Field of Classification Search
CPC .............. A61B 5/0022; A61B 5/14532; A61B 2560/0475; A61B 2560/0271;
(Continued)

(56) References Cited

U.S. PATENT DOCUMENTS 7,912,674 B2    3/2011    Clark et al.
9,967,739 B2    5/2018    Proennecke et al.
(Continued)

FOREIGN PATENT DOCUMENTS

WO    WO 2001/52727 A1    7/2001

OTHER PUBLICATIONS

International Application No. PCT/EP2016/062673 International Search Report and Written Opinion, dated Oct. 7, 2016.

*Primary Examiner* — Nathan R Price
*Assistant Examiner* — Anh Bui
(74) *Attorney, Agent, or Firm* — Woodard, Emhardt, Henry, Reeves & Wagner LLP

(57) ABSTRACT

The invention provides for a medical system comprising a control unit and a medical appliance. The medical appliance comprises: a first processor and a monitoring system for measuring an analyte concentration subcutaneously. The control unit comprises a second processor and a second memory with a persistent partition and an application partition containing a medical application and application data comprising a medical data entry. The medical application backs up the application data as archived data in the persistent partition. The first processor is programmed to: record the analyte concentration, generate the medical data entry using the analyte concentration, and transfer the medi-
(Continued)

cal data entry to the control unit. The second memory further contains an operating system operable for de-installing the medical application without deleting the archived data.

13 Claims, 3 Drawing Sheets

(51) Int. Cl.
*A61B 5/145* (2006.01)
*G16H 10/60* (2018.01)
*A61M 5/168* (2006.01)
*A61B 5/1486* (2006.01)
*A61M 5/142* (2006.01)
*G16H 40/40* (2018.01)
*G16H 50/20* (2018.01)
*G06F 19/00* (2018.01)
*A61B 5/1495* (2006.01)
*G16H 40/63* (2018.01)

(52) U.S. Cl.
CPC ...... *A61B 5/14532* (2013.01); *A61B 5/14865* (2013.01); *A61M 5/14248* (2013.01); *A61M 5/16827* (2013.01); *A61M 5/1723* (2013.01); *G16H 10/60* (2018.01); *G16H 40/40* (2018.01); *G16H 50/20* (2018.01); *A61B 5/1495* (2013.01); *A61B 2560/0214* (2013.01); *A61B 2560/0475* (2013.01); *A61M 2005/1726* (2013.01); *A61M 2205/3561* (2013.01); *A61M 2205/3569* (2013.01); *A61M 2205/52* (2013.01); *A61M 2205/8206* (2013.01); *A61M 2230/201* (2013.01); *G06F 19/3468* (2013.01); *G16H 40/63* (2018.01)

(58) Field of Classification Search
CPC ... A61M 2205/52; G16H 40/40; G16H 50/20; G16H 10/60
See application file for complete search history.

(56) References Cited

U.S. PATENT DOCUMENTS

| | | |
|---|---|---|
| 10,111,588 B2 | 10/2018 | Tankiewicz et al. |
| 2008/0119705 A1 | 5/2008 | Patel et al. |
| 2008/0287885 A1 | 11/2008 | Hoffmann et al. |
| 2009/0058635 A1 | 3/2009 | LaLonde et al. |
| 2011/0184264 A1 | 7/2011 | Galasso et al. |
| 2011/0256024 A1 | 10/2011 | Cole et al. |
| 2014/0012117 A1 | 1/2014 | Mensinger et al. |

MEASUREMENT SYSTEM FOR MEASURING THE CONCENTRATION OF AN ANALYTE WITH A SUBCUTANEOUS ANALYTE SENSOR

FIELD OF THE INVENTION

The invention relates to medical instrumentation, in particular to analyte sensors for measuring an analyte concentration of a subject using a subcutaneous analyte sensor.

BACKGROUND AND RELATED ART

The maintenance of certain chronic diseases may require a subject to accurately monitor an analyte level to maintain optimal health. For example diabetic need to accurately monitor blood glucose levels to maintain proper health. The journal article Lodwig, Volker, et al. "Current trends in continuous glucose monitoring." Journal of diabetes science and technology 8.2 (2014): 390-396 discusses some current issues with glucose monitoring.

International patent application WO 2006076930 discloses devices for sensing a concentration of chemical constituents in body fluid such as interstitial fluid, including but not limited to glucose. The devices also relates to systems for measuring and reporting the concentration of body fluid constituents at time intervals shorter than the physiological response time, thereby providing effectively continuous concentration measurements. The device according to the present invention comprises a probe, a reservoir with perfusion fluid connected to an inlet of the probe, at least one test zones which comprise a reagent, to react with the analyte to produce a detectable change, a reader unit which reads test zones wetted with fluid containing the analyte, where the reader unit produces signals according to the concentration of the analyte in the fluid; and a processing unit for processing the signals and the concentration of the analyte.

United States patent application US 20110053121 A1 discloses a system and method for monitoring individual metabolic response and for generating nutritional feedback involve monitoring of a glucose level in a qualified subject. The method comprises the step of consecutively performing a plurality of measurements of a glucose level in the qualified subject by a measuring device. In the measuring device first data corresponding to the measured glucose level is generated. This data is further transmitted to an analysis device. There, second data is generated representing at least one measure for variability of a glucose level of the subject from a time-series of glucose measurements represented by the first data. The second data is compared with reference data and a result of the comparison is further processed for generating a conclusion about nutritional quality of foodstuffs consumed by the subject and/or about a risk of long-term health complications of the subject. Finally, feedback is provided corresponding to the conclusion on an output device.

United States patent U.S. Pat. No. 6,434,409 B1 discloses a method for determining and monitoring tissue glucose concentration. Additionally, the present invention concerns a measuring apparatus to determine and monitor glucose concentration.

SUMMARY

The invention provides for a medical system in the independent claims. Embodiments are given in the dependent claims.

In one aspect the invention provides for a medical system comprising a control unit and a medical appliance. In various examples the medical appliance may comprise different medical components. For example the medical appliance could comprise a continuous glucose monitoring or CGM system. In other examples the medical appliance could also or alternatively include a pump system for supplying a fluid to a subject. The CGM system could for example comprise a control unit that is a smartphone or a remote control system. It may also include a body-mounted patch with a sensor for measuring glucose values in interstitial tissue; it may also comprise a transmitter for receiving the measured glucose values. The transmitter may also be used for optionally calibrating the medical appliance for measured glucose values to blood glucose values. The pump system could comprise the control unit such as a smartphone or remote control with a fluid reservoir and a pump. The fluid reservoir could be used to supply insulin and/or glucagon. The fluid reservoir may be connected to a pump and an infusion set with an infusion needle.

In some embodiments the medical appliance is a body-worn medical appliance. For example the medical appliance could be attached to an article of clothing or a strap or harness system that is used to attach it to the body. In other examples the body-worn medical appliance could be attached to a subject with an adhesive or an adhesive layer. The medical appliance further comprises a subcutaneous portion. In different examples the subcutaneous portion could take different forms. For example the subcutaneous portion could be a sensor in a CGM system. In a pump or infusion system the needle or cannula may be the subcutaneous portion. In further examples there may be one or more cannulas and one or more sensors.

The medical appliance is powered by a first battery. The medical appliance comprises a first wireless communication module. The wireless communication module could take different forms. For example it could be a wireless or Wi-Fi connection. In other examples it may be a Bluetooth communication module. The medical appliance comprises a first processor and a first memory. The first memory contains medical appliance instructions for operating the medical appliance. The medical appliance comprises a monitoring system. In some examples the monitoring system may be a continuous monitoring system. In other examples the monitoring system monitors intermittently. The monitoring system comprises a sensor for measuring an analyte concentration. The subcutaneous portion comprises at least a portion of an analyte sensor.

In some embodiments the control unit is powered by a second battery. The control unit further comprises a second wireless communication module. The first and second wireless communication modules are able to exchange wireless communication and messages. The control unit comprises a second processor and a second memory. The second memory comprises an application partition and a persistent partition. The application partition contains a medical application and application data. The persistent partition contains archive data. The archive data comprises a copy of at least a portion of the application data.

The first wireless communication module and the second wireless communication module are operable for forming a wireless communication channel between the medical appliance and the control unit. The wireless communication channel may be used for exchanging instructions and data between the medical appliance and the control unit.

The medical application is configured for controlling the medical appliance by sending messages to the first processor via the wireless communication channel.

In some examples the data is first modified or stored in the application partition and then it is later copied or updated on the persistent partition.

In another embodiment the medical data entry comprises an analyte concentration. Execution of the medical appliance instructions causes the first processor to record the analyte concentration using the monitoring system. Execution of the medical appliance instructions further cause the first processor to generate a medical data entry at least partially using the analyte concentration. Execution of the medical appliance instructions further cause the first processor to transfer the medical data entry to the control unit using the wireless communication channel. The application data comprises the medical data entry.

In another embodiment the second memory further contains an operating system. The operating system is operable for de-installing the medical application. The de-installation deletes the application data and preserves the archive data on the persistent partition.

The potential advantage is that the data on the persistent partition is persistently available even if the medical application has been de-installed. This may be beneficial because it may provide access to the data even if the application has been de-installed and possibly reinstalled. This may facilitate diagnosis or repair of the medical system and may also provide access to e.g. the analyte concentrations if the medical application is de-installed.

For example, a user may trouble with the operation of the medical system and may decide to uninstall the medical application and then re-install it. If the archive data were stored in the application partition it would be lost. Having the archive data stored in the persistent partition may allow a technician or other user to study the archive data during the investigation of a fault or failure of the medical system, even if the medical application has been deinstalled.

In another example, the control unit could be a smart phone, tablet, or other mobile computing device. The installing of other software could in some instances result in the other software interfering with the function of the medical application. The user of the control unit my therefore repeatedly install and de-install many other applications or apps. The medical application could store data which relates to the state or configuration of the control unit periodically or when errors occur and store this configuration data in the archive data. This may facilitate the repair or diagnosis of the medical system.

In another example, the medical application could store metadata or data in the archive data which is descriptive of the use and/or configuration of the medical application. This may include data descriptive of failures, details about the installation and/or de-installation of the medical application, and data descriptive of the use of the medical application. This may further aid the diagnosis and/or repair of the medical system.

Overall having log, system and/or medical data persistently available in the persistent partition allows to use such data even if the application is de-installed or re-installed. For instance the medical data is not lost and may still be accessed by the user or an health care practitioner after de-installation. Furthermore, upon re-installation system data may be recovered. Such system data may include configuration data such as pairing keys between the medical appliance and the control unit that may be recovered to re-establish connection between the two devices. Similarly system data such as encryption keys may be recovered and re-used. Lastly, log data allows identifying any errors or warnings or failures of the control unit or medical appliance even after de-installation. This is particularly useful for any investigations into the system after its usage.

In another embodiment the control unit further comprises a data exchange interface for exchanging data with a computer system. The computer system for example may be located locally to the control system or it may be located remotely in a network system. The application data and/or the archive data is accessible to the computer system via the data exchange interface.

In the case faults, errors or wrong user handling and so on important data can always be accessed by a healthcare practitioner (HCP) or IT services from the provider. This may provide a further security measure for a medical system. It may be advantageous to be able to access the archive data when the medical application is de-installed. In some examples this data may also be stored or located on a cloud or other systems that are accessible via a data network.

In another embodiment the medical appliance comprises an electronic portion. The electronic portion comprises the first processor, the first memory, and the first battery.

In another embodiment the medical appliance instructions comprise a first set of pairing instructions. The application data comprises a second set of pairing instructions. The archive data comprises the second set of pairing instructions. Execution of the first set of pairing instructions by the first processor and execution of the second set of pairing instructions by the second processor cause the first wireless communication module to pair with the second communication module to form the wireless communication channel. The medical application is configured for searching the first system partition for the second set of pairing instructions upon being reinstalled. The medical application is configured for re-establishing the wireless communication channel if the second set of pairing instructions are detected.

In another embodiment the control unit establishes a pairing with the medical appliance. The first set of pairing instructions of the control unit are executed from the first memory and the second set of pairing instructions on the medical appliance are executed from the second memory. The medical application on the control unit may store data or information that duplicates the pairing information such as keys, address data and various components. This may be done in the archived data in the persistent partition. Upon loss of the pairing between the medical appliance and the control unit can then re-use this data in order to re-establish the pairing without any interaction between the medical appliance and the control unit.

In another embodiment the medical appliance instructions cause the first processor to generate the first set of pairing instructions according to a first wireless pairing protocol portion. The medical application causes the second processor to generate the second set of pairing instructions according to a second wireless pairing protocol portion. The first wireless pairing protocol portion and the second wireless pairing protocol portion form a complete wireless pairing protocol. Generation of the first set of pairing instructions causes the first processor to disable the first wireless pairing protocol portion.

In another embodiment the application data comprises at least one data entry including a log data entry, the medical data entry, and/or a system data entry. Execution of the medical application causes the second processor to generate the data entry. The second processor may take a log data entry, medical data entry and/or a system data entry and use this to generate the data entry. Execution of the medical application further causes the second processor to append the data entry to the application data. Execution of the medical application further causes the second processor to append the data entry to the archive data.

The archive data may comprise various types of information. It may for instance comprise medical data such as CGM data or other measurements. The archive data may also comprise log data that may be used for service and for fault or failure investigation. For example in the case of sensor errors or warnings or failures of the control unit or medical appliance. Archive data may also comprise system data for example pairing information such as keys, identifications or cryptographic keys or information.

The log data may comprise various components. For example it may have logs of both the control unit and/or the medical appliance. Logs of both system components are stored on the control unit. Such logs may be kept in the first application partition as long as the medical application is installed. Additionally, this data may be copied or written to the system partition in order to keep this information available in case the medical application is de-installed.

In another embodiment execution of the medical application causes the second processor to generate a message in response to a control unit malfunction or a medical appliance malfunction. The log data entry is generated at least partially using the error message.

In another embodiment execution of the medical application causes the second processor to generate a system log descriptive of a hardware configuration of the control unit and/or a software configuration of the control unit. The system data entry is generated at least partially using the system log.

In another embodiment execution of the medical application further causes the second processor to encrypt the data entry with an encryption key before appending the data entry to the application data.

In another embodiment execution of the medical application causes the second processor to encrypt the archive data.

In another embodiment the encryption key for the log data entry and/or the system data entry is a public key of an asymmetric key pair.

In another embodiment the encryption key for the medical data entry is the private key of a symmetric key pair. The use of a public key is beneficial because if the control unit is lost there is no private or decryption key on the control unit. This may be used to provide authenticity of the data and also to protect it from being read in an unauthorized manner.

In another embodiment only the public key of the symmetric key pair is stored in the second memory of the control unit.

In another embodiment the private key of the symmetric key pair is stored on a remote computer system that is able to retrieve the application data and/or the archive data via the data exchange interface.

In another embodiment the control unit is a mobile telephone device.

In another embodiment the mobile telephone device comprises a subscriber identity module for enabling access to a mobile telecommunications network. The subscriber identity module comprises a SIM processor. The subscriber identity module further comprises a protected memory for storing the encryption key. The encryption key may be the public key. The second processor encrypts the data entry by transferring the unencrypted log entry to the subscriber identity module and receiving the encrypted log entry from the subscriber identity module.

In another embodiment the control unit is a handheld device and may use for example wireless LAN, USB or other techniques for transferring data via the data exchange interface.

In another embodiment the medical appliance comprises a monitoring system. The monitoring system comprises a sensor for measuring the analyte concentration. The subcutaneous portion comprises at least a portion of an analyte sensor and wherein the execution of the control instructions causes the second processor to control the monitoring system via the wireless communication channel.

In another embodiment the subcutaneous portion comprises at least a portion of a glucose sensor. The medical appliance comprises a glucose monitoring system.

In another embodiment the subcutaneous portion comprises at least one cannula. The medical appliance comprises a pumping system.

In another embodiment the pumping system comprises an insulin pump for pumping insulin through the at least one cannula.

In another embodiment the pumping system further comprises a glucagon pump for pumping glucagon through the at least one cannula.

In another embodiment the pumping system comprises both an insulin pump and a glucagon pump.

In another embodiment execution of the control instructions further causes the second processor to control the pumping system via the wireless communication channel.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
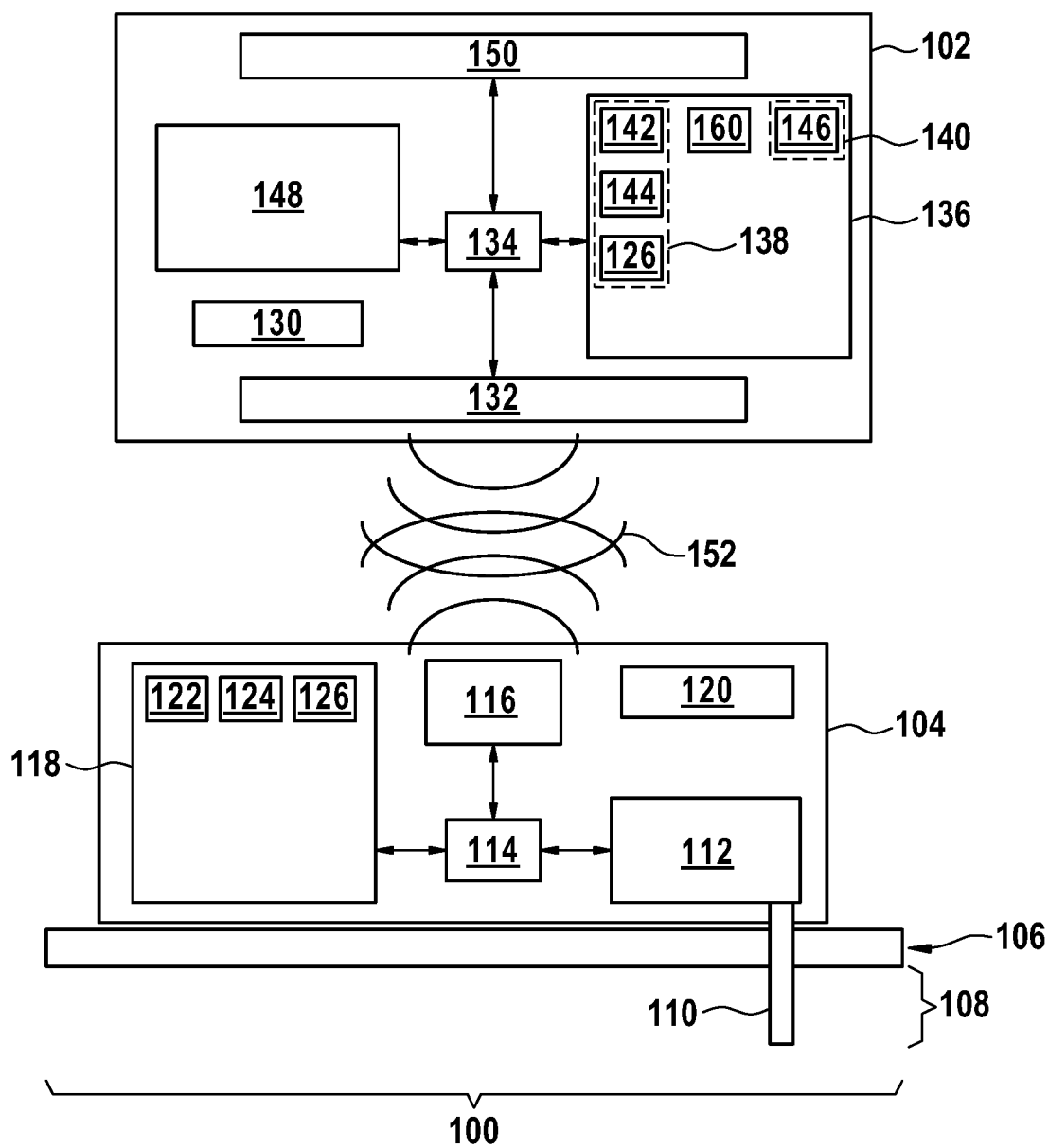
FIG. 1 illustrates an example of a medical system.

FIG. 1 shows an example of a medical system 100. The medical system 100 comprises a control unit 102 and a medical appliance 104. In this example the medical appliance 104 is seen as being attached to the skin 106 of a subject. Below the skin is a subcutaneous region 108 of the subject. The medical appliance 104 has a subcutaneous portion 110 that extends through the skin 106 into the subcutaneous 108. The subcutaneous portion 110 may represent one or more cannula and/or it may represent one or more sensors which are inserted into the subcutaneous region 108. The subcutaneous portion 110 is seen as being connected to a medical module 112.

The medical module may comprise one or more monitoring systems for recording data from the one or more sensors and the medical module 112 may also comprise one or more pumps with reservoirs for pumping fluid such as insulin or glucagon into the subcutaneous region 108 via one or more cannulas. The medical module 112 is seen as being controlled by a first processor 114. The first processor 114 is further shown as being connected to a first wireless communication module 116 and a first memory 118. The medical appliance 104 is powered by a first battery 120. The first memory 118 is shown as containing medical appliance instructions 122. The medical appliance instructions 122 comprise instructions which enable the first processor 114 to operate the medical appliance 104.

The medical appliance instructions 122 may for instance contain commands for controlling the medical module 112 and for getting the first wireless communication module 116 to communicate with the control unit 102. The first memory 118 is further shown as containing an analyte concentration 124 that was measured using a sensor that is part of the subcutaneous portion 110. The first memory 118 is further shown as containing a medical data entry 126 that was constructed at least partially using the analyte concentration 124.

The control unit 102 is shown as comprising a second battery 130 which is used to power the control unit 102. The control unit 102 further comprises a second wireless communication module 132. The second wireless communication module 132 is shown as being connected to a second processor 134. The second processor is also connected to a second memory 136 and a data exchange interface 150. The data exchange interface 150 may be used to communicate with other communication networks or computers or controllers. The data exchange interface 150 may be optional in some examples. The second memory 136 is shown as having an application partition 138 and a persistent partition 140. Within the application partition 138 there is a medical application 142. The medical application 142 contains instructions which enable the processor 134 to run a control program for controlling the medical appliance 104. The application partition 138 is further shown as containing application data 144. The application data may comprise such information as medical data and logs and other information associated with the control unit 102 controlling the medical appliance 104. The application partition 138 is further shown as containing a medical data entry 126 that was received from the medical appliance 104. In FIG. 1 the first wireless communication module 116 and the second wireless communication module 132 are shown as a wireless communication channel 152. The first processor 114 transferred the medical data entry 126 to the second processor 134 via the wireless communication channel 152.

The persistent partition 140 is shown as containing archive data 146. The archive data may for instance contain portions of the medical data entry 126 or other information such as log or error messages or configuration commands for configuring the wireless communication channel 152.

The archive data 146 may contain various types of information or data. As previously mentioned it may contain medical data, error messages, and log data. It may also contain data or metadata which is descriptive of the system state or configuration of the medical system 100. For example other application or apps may be installed in the control unit 102. Storing this information in the archived data may be useful, because if there are faults or failures of the medical system a user may start to install and/or de-install other programs. Recoding data descriptive of the configuration of the medical system, and the control unit 102 in particular may assist in the diagnosis of failures or faults of the control unit 102 and/or medical system 100.

The second memory 136 is further shown as containing an operating system 160. The operating system 160 is operable for de-installing the medical application 142. The de-installation process deletes the application data 144 and may remove the entire contents of the application partition 138 or also the application partition 138 itself. During the de-installation process the operating system 160 preserves the persistent partition 140 and does not remove the archive data 146. If the medical application 142 is de-installed and then reinstalled the archive data 146 will still be present in the persistent partition 140.

Figure 2:
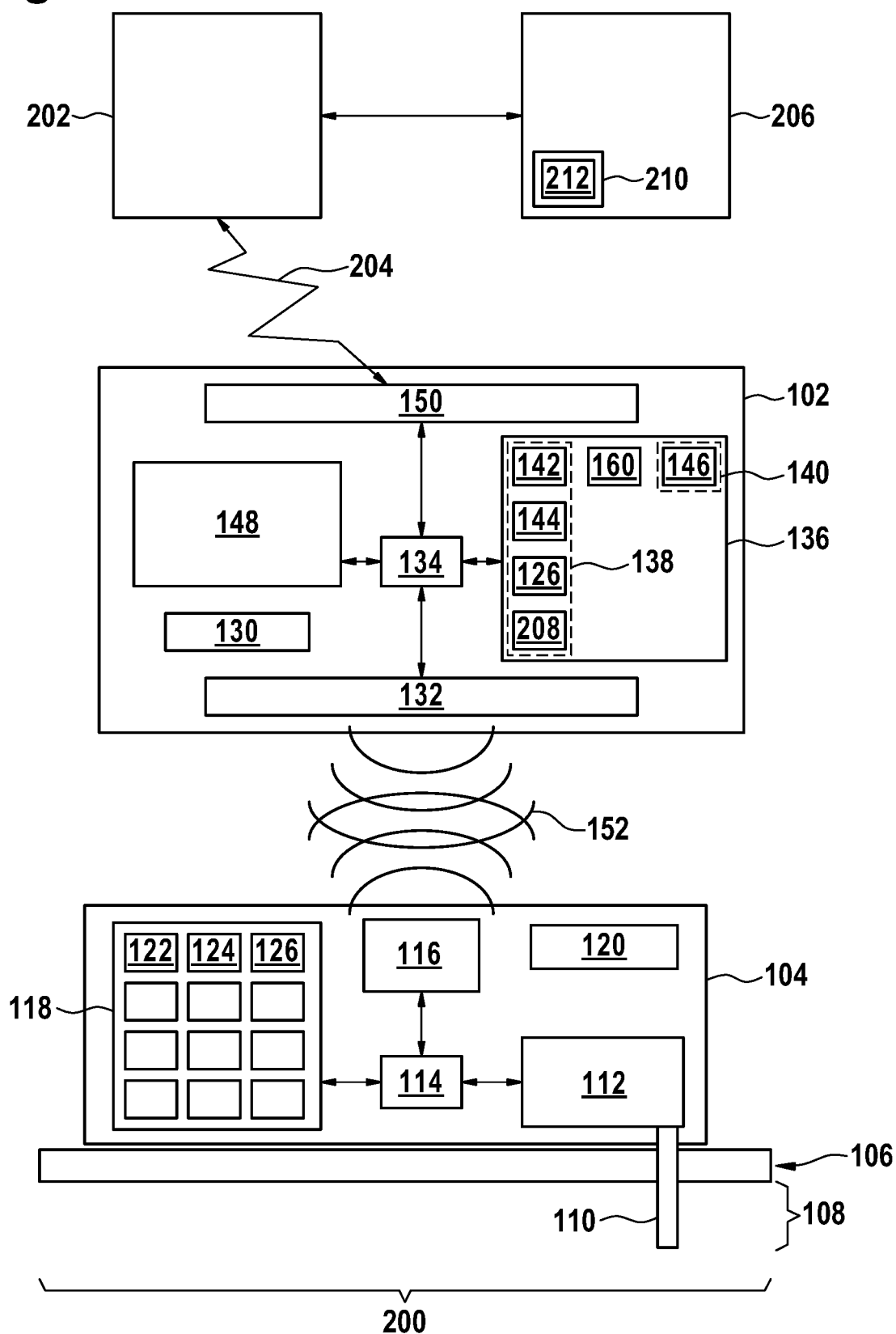
FIG. 2 illustrates a further example of a medical system.

FIG. 2 shows a further example of a medical system 200. The medical system 200 shown in FIG. 2 is similar to the medical system 100 of FIG. 1 with several additional components and features shown. In the example shown in FIG. 2 the exchange interface 150 may be a subscriber identity module for enabling access to a mobile telephone communications network 202. The subscriber identity module 150 is shown as having formed a network connection 204 with the mobile telephone communications network 202. The mobile telephone communications network 202 is shown as being connected to a remote server 206. The second processor 134 may be able to transfer the archive data 146 to the remote server 206 using the network connection 204.

In an alternative the application partition 138 may store a public key 208 which may be used to either sign and/or to encrypt the archive data 146. The signed and/or encrypted archive data 146 may then be transferred securely from the second processor 134 to the remote server 206. The remote server 206 is shown as having a private key 212 stored in a remote storage 210. This enables the remote server 206 to either authenticate or decrypt the archive data 146. As the private key 212 is not stored on the control unit 102 there is no danger of the archive data 146 being compromised if the control unit 102 is lost or stolen.

Figure 3:
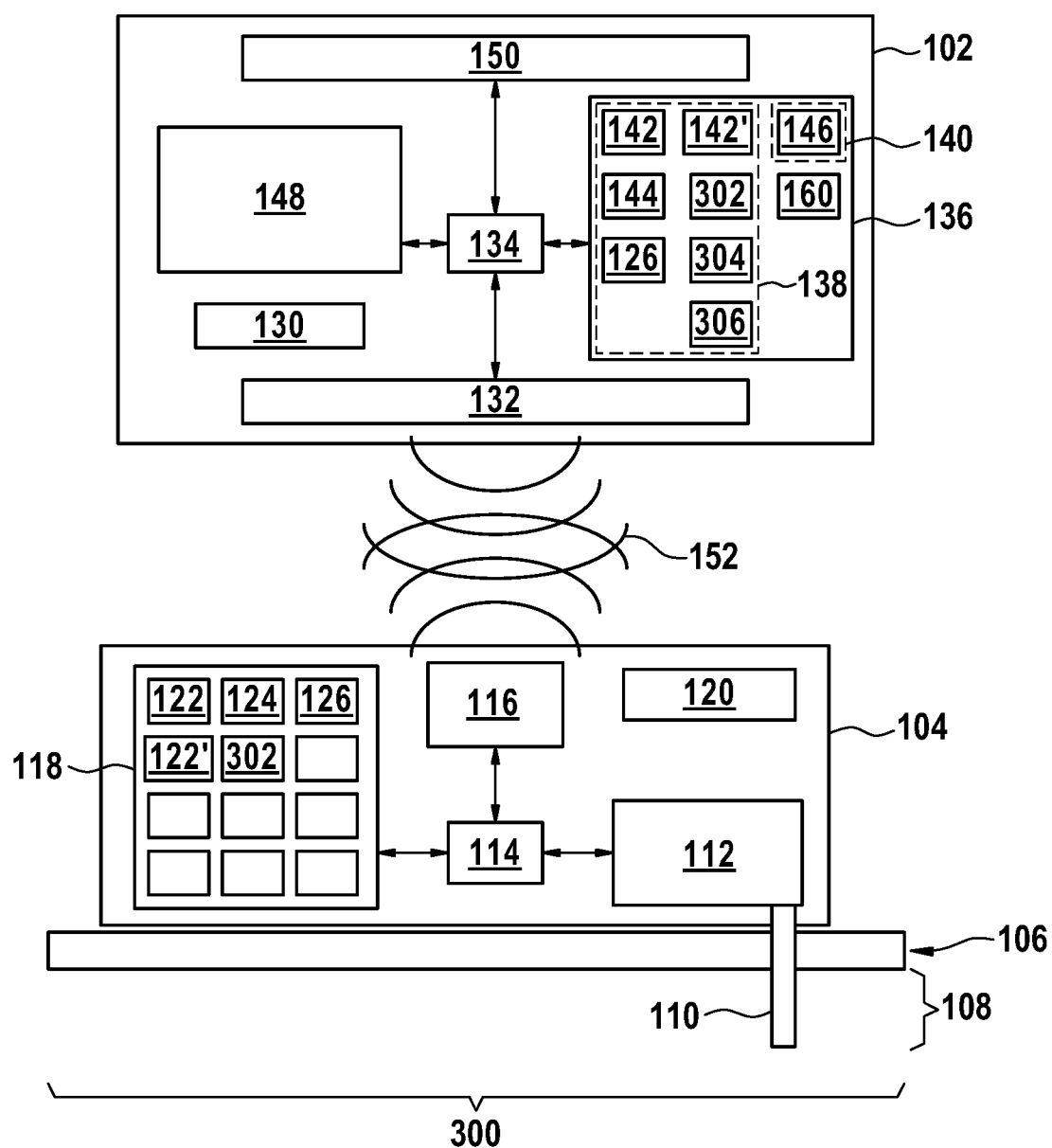
FIG. 3 illustrates a further example of a medical system.

FIG. 3 shows a further example of a medical system 300. The medical system 300 shown in FIG. 3 is similar to that shown in FIG. 1 with the addition of several features. The features of the medical systems 200 and 300 shown in FIGS. 2 and 3 may be combined.

The first memory 118 of the medical system 300 is shown as containing first pairing instructions 122' which are part of the medical appliance instructions 122. The first pairing instructions 122' contain instructions which enable the processor 114 to control the first wireless communication module 116 to pair with the second wireless communication module 132. The application partition 138 is further shown as containing second pairing instructions 142' that are used by the second processor 134 to control the second wireless communication module 132 to pair with the first wireless communication module 116. The medical application 142 may copy the second pairing instructions 142' into the archive data 146. This may have the advantage that if the medical application is de-installed 142 and then reinstalled the second pairing instructions 142' may still be available and accessible to the processor 134. This may enable the control unit 102 to pair with the medical appliance 104 without the exchange of any communication. In some examples the second pairing instructions 142' may be stored within the system partition 140 separate from the archive data 146. For example the archive data 146 may be encrypted by a key which is not accessible to the processor 134. In this case the second pairing instructions 142' are stored separately from the archive data 146.

In this example the first memory 118 is further shown as containing first log data 302. The first log data 302 may contain records on the usage of the medical appliance 104 and/or failure data of the medical appliance 104. This may be transferred via the wireless communication link 152 to the application partition 138. The application partition 138 is further shown as containing second log data 304 which may contain configuration information about the medical application 142 and/or failures of the medical application 142. The medical application 142 may append the first log data 302 and/or the second log data 304 to a data entry 306. The data entry 306 may be appended to the archive data 146.

LIST OF REFERENCE NUMERALS 100 medical system
102 control unit
104 medical appliance
106 skin
108 subcutaneous region
110 subcutaneous portion (sensor)
112 medical module (monitoring system)
114 first processor
116 first wireless communication module
118 first memory
120 first battery
122 medical appliance instructions
122' first pairing instructions
124 analyte concentration
126 medical data entry
130 second battery
132 second wireless communication module
134 second processor
136 second memory
138 application partition
140 persistent partition
142 medical application
142' second paring instructions
144 application data
146 archived data
148 user interface
150 data exchange interface
152 wireless communication channel
160 operating system
200 medical system
202 mobile telephone communications network
204 network connection
206 remote server
208 public key
210 remote storage
212 private key
300 medical system
302 first log data
304 second log data
306 data entry

The invention claimed is:

1. A medical system comprising a control unit and a medical appliance,
wherein the medical appliance is a body-worn medical appliance, wherein the medical appliance comprises a subcutaneous portion, wherein the medical appliance is powered by a first battery, wherein the medical appliance comprises a first wireless communication module, wherein the medical appliance comprises a first processor and a first memory, wherein the first memory contains medical appliance instructions for operating the medical appliance, wherein the medical appliance comprises a monitoring system, wherein the monitoring system comprises a sensor for measuring an analyte concentration, wherein the subcutaneous portion comprises at least a portion of an analyte sensor;

wherein the control unit is powered by a second battery, wherein the control unit further comprises a second wireless communication module, wherein the control unit comprises a second processor and a second memory, wherein the second memory comprises an application partition and a persistent partition, wherein the application partition contains a medical application and application data, wherein the persistent partition contains archived data, wherein the archived data comprises a copy of at least a portion of the application data;

wherein the first wireless communication module and the second wireless communication module are operable for forming a wireless communication channel between the medical appliance and the control unit;

wherein the medical application is configured for controlling the medical appliance by sending messages to the first processor via the wireless communication channel, wherein execution of the controller instructions cause the second processor to control the monitoring system via wireless communication channel, wherein the medical application is configured for modifying the application data in the application partition and storing the portion of the application data comprised in the archived data in the persistent partition;

wherein the medical data entry comprises the analyte concentration, wherein execution of the medical appliance instructions cause the first processor to:

record the analyte concentration using the monitoring system, generate a medical data entry at least partially using the analyte concentration, and transfer the medical data entry to the control unit using the wireless communication channel, wherein the application data comprises the medical data entry; and wherein the second memory further contains an operating system, wherein the operating system is operable for de-installing the medical application, wherein the de-installation deletes the application data and preserves the archived data on the persistent partition.

2. The medical system of claim 1, wherein the control unit further comprises a data exchange interface for exchanging data with a computer system, wherein the application data and/or archived data is accessible to the computer system via the data exchange interface.

3. The medical system of claim 1, wherein the medical appliance instructions comprise a first set of pairing instructions, wherein the application data comprises a second set of pairing instructions, wherein the archived data comprises the second set of pairing instructions, wherein execution of the first set of pairing instructions by the first processor and execution of the second set of pairing instructions by the second processor cause the first wireless communication module to pair with the second communication module to form the wireless communication channel, wherein the medical application is configured for searching the persistent partition for the second set of pairing instructions upon being re-installed, wherein the medical application is configured for re-establishing the wireless communication channel, if the second set of pairing instructions are detected.

4. The medical system of claim 1, wherein the application data comprises at least one data entry including a log data entry, the medical data entry, and/or a system data entry; wherein execution of the medical application causes the second processor to:
- generate the data entry;
- append the data entry to the application data; and
- append the data entry to the archived data.

5. The medical system of claim 1, wherein execution of the medical application causes the second processor to generate an error message in response to a control unit malfunction or a medical appliance malfunction, wherein the log data entry is generated at least partially using the error message.

6. The medical system of claim 1, wherein execution of the medical application causes the second processor to generate a system log descriptive of a hardware configuration of the control unit and/or a software configuration of the control unit, wherein the system data entry is generated at least partially using the system log.

7. The medical system of claim 1, wherein execution of the medical application further causes the second processor to encrypt the data entry with an encryption key before appending the data entry to the application data.

8. The medical system of claim 1, wherein execution of the t Medical application causes the second processor to encrypt the archived data.

9. The medical system of claim 7, wherein the encryption key for the log data entry and/or the system data entry is a public key of an asymmetric key pair.

10. The medical system of claim 7, wherein the encryption key for the medical data entry is a public key of a symmetric key pair.

11. The medical system of claim 1, wherein the subcutaneous portion comprises at least a portion of a glucose sensor, wherein the medical appliance comprises a glucose monitoring system.

12. The medical system of claim 1, wherein the subcutaneous portion comprises at least one cannula, wherein the medical appliance comprises a pumping system.

13. The medical system of claim 12, wherein the pumping system comprises anyone one of the following: an insulin pump for pumping insulin through the at least one cannula, a glucagon pump for pumping glucagon through the at least one cannula, and combinations thereof; and wherein execution of the controller instructions cause the second processor to control the pumping system via wireless communication channel.

* * * * *